US009949795B2

United States Patent
Nino et al.

(10) Patent No.: US 9,949,795 B2
(45) Date of Patent: *Apr. 24, 2018

(54) FORTIFIED PLASTIC CONNECTOR MOUNT FOR DISPOSABLE DEVICES

(71) Applicant: ECA Medical Instruments, Newbury Park, CA (US)

(72) Inventors: John Nino, Simi Valley, CA (US); David Ivinson, Camarillo, CA (US)

(73) Assignee: ECA MEDICAL INSTRUMENTS, Newbury Park, CA (US)

( * ) Notice: Subject to any disclaimer, the term of this patent is extended or adjusted under 35 U.S.C. 154(b) by 207 days.

This patent is subject to a terminal disclaimer.

(21) Appl. No.: 14/806,182

(22) Filed: Jul. 22, 2015

(65) Prior Publication Data

US 2015/0320502 A1 Nov. 12, 2015

Related U.S. Application Data

(63) Continuation of application No. PCT/US2014/011719, filed on Jan. 15, 2014.

(Continued)

(51) Int. Cl.
| | |
|---|---|
| *A61B 19/00* | (2006.01) |
| *B25B 23/14* | (2006.01) |
| *A61B 17/88* | (2006.01) |
| *A61B 90/00* | (2016.01) |

(Continued)

(52) U.S. Cl.
CPC .......... *A61B 19/30* (2013.01); *A61B 17/8875* (2013.01); *A61B 90/03* (2016.02);
(Continued)

(58) Field of Classification Search
CPC ............ B25B 23/1415; B25B 23/1427; B25B 23/141; B25B 15/04; B25B 23/0042;
(Continued)

(56) References Cited

U.S. PATENT DOCUMENTS

| | | |
|---|---|---|
| 6,132,435 A | 10/2000 | Young |
| 2006/0179981 A1 | 8/2006 | Cutler et al. |

(Continued)

FOREIGN PATENT DOCUMENTS

| | | |
|---|---|---|
| JP | 2001-311219 A | 11/2001 |
| WO | WO 2003/013372 A2 | 2/2003 |
| WO | WO 2012/112812 A2 | 8/2012 |

OTHER PUBLICATIONS

International Patent Application No. PCT/US2014/011719; Int'l Preliminary Report on Patentability; dated Aug. 6, 2015; 12 pages.

(Continued)

*Primary Examiner* — Robert Scruggs
(74) *Attorney, Agent, or Firm* — Baker & Hostetler LLP (57) ABSTRACT

Disclosed herein is a fortified plastic connector mount having a plastic generally conical nose with a top and bottom, the bottom formed as part of or affixed to the flat top of a body and the top of the nose having a square channel guide with corners. The channel is formed axial and centered in the nose and of a size to accept a tool or shaft. At 90 degree orientation from each other are four pairs of force buttressing ribs "FBR" wherein the FBR have a bottom affixed at said flat top, and the FBR has a support edge affixed to an annular outer wall of the nose. The four pairs of FBR each pair being positioned along one of the four sides of the square channel. In some instances, each FBR further comprises an interior edge and an outer edge and each outer edge is aligned with a corner.

12 Claims, 9 Drawing Sheets

Related U.S. Application Data (60) Provisional application No. 61/755,640, filed on Jan. 23, 2013.

(51) Int. Cl.
*B25G 3/32* (2006.01)
*B25B 23/00* (2006.01)
*A61B 17/00* (2006.01)
*A61C 8/00* (2006.01)

(52) U.S. Cl.
CPC ...... *B25B 23/0035* (2013.01); *B25B 23/0042* (2013.01); *B25B 23/1415* (2013.01); *B25G 3/32* (2013.01); *A61B 2017/00526* (2013.01); *A61B 2090/031* (2016.02); *A61C 8/0089* (2013.01)

(58) Field of Classification Search
CPC .......... A61B 17/8875; A61B 2090/031; A61B 2090/037; A61B 90/03
See application file for complete search history.

(56) References Cited

U.S. PATENT DOCUMENTS

| | | |
|---|---|---|
| 2006/0254392 A1 | 11/2006 | Frank |
| 2006/0278051 A1 | 12/2006 | Gauthier et al. |
| 2010/0274230 A1* | 10/2010 | Edgell ................. A61N 1/3752 606/1 |
| 2012/0198972 A1* | 8/2012 | Nino ...................... B25B 15/04 81/471 |

OTHER PUBLICATIONS

International Patent Application No. PCT/US2014/011719; Int'l Search Report and the Written Opinion; dated May 1, 2014; 16 pages.

European Patent Application No. 14743262.9; Extended Search Report; dated Mar. 3, 2017; 7 pages.

\* cited by examiner

FORTIFIED PLASTIC CONNECTOR MOUNT FOR DISPOSABLE DEVICES

CROSS REFERENCE TO RELATED APPLICATIONS

This Utility patent application is a Continuation of International patent application PCT/US2014/011719 filed Jan. 15, 2014, which claims the full Paris Convention benefit of and priority to U.S. provisional application No. 61/755,640 filed Jan. 23, 2013, the contents of which are incorporated by this reference as if fully set forth herein in their entirety.

BACKGROUND

1. Field

This disclosure relates to a plastic disposable mount fortified to withstand higher forces applied to a shaft.

2. General Background

Torque drivers and torque limiting drivers are widely used throughout manufacturing, assembly and the medical industry. Torque-limiting drivers have a factory pre-set torque to ensure the accuracy and toughness required to meet a demanding surgical environment. Disposable torque drivers are often rated to withstand a maximum rotational force applied thereto before the mounting of a drive tool fails.

The medical industry has made use of both reusable and disposable torque-limiting drivers. In a surgical context, there is little room for error and these drivers must impart a precise amount of torque.

Reusable drivers require constant recalibration to ensure that the driver is imparting the precise amount of torque. Recalibration is a cumbersome task, but must be done routinely.

Disposable drivers are an easy to use and reliable alternative to the reusable drivers. Typically, a medical device such as an implant, for example, is packaged with a disposable driver designed to the implant's specifications. Once the driver has been used, it can be discarded. Thus, a surgeon can have complete confidence that the disposable driver, packaged with an implant, will impart either the precise amount of torque required or at least the amount of torque required (for fixed devices). Typically, the torque requirement is different for different operations and for different implants. For example, applications may include those in the field of orthopedic surgery, construction and emplacement of implants, etc.

These disposable drivers have been used for low torque applications. The standard torque values in these applications typically range from 4 to 20 inch-ounces. It has, however, been a challenge to develop a reliable disposable driver capable of imparting higher torques for larger applications.

DISCLOSURE

Torque is a measure of how much force acting on an object causes that object to rotate. In the case of a driver and a fastener, this measurement can be calculated mathematically in terms of the cross product of specific vectors:

$$\tau = r \times F$$

Where r is the vector representing the distance and direction from an axis of a fastener to a point where the force is applied and F is the force vector acting on the driver.

Torque has dimensions of force times distance and the SI unit of torque is the Newton meter (N m). The joule, which is the SI unit for energy or work, is also defined as an Nm, but this unit is not used for torque. Since energy can be thought of as the result of force times distance, energy is always a scalar whereas torque is force cross-distance and so is a vector-valued quantity. Other non-SI units of torque include pound-force-feet, foot-pounds-force, ounce-force-inches, meter-kilograms-force, inch-ounces or inch pounds.

A fortified plastic connector mount, in accordance with the present disclosure, has a handle, a body and a work-piece engaging tip. Within the cylindrical body there is a torque-limiting assembly. The torque-limiting assembly includes an upper cylindrical shank and a lower cylindrical shank. The upper cylindrical shank and the lower cylindrical shank have a plurality of teeth. The teeth have a vertical face, an inclined face and a substantially flat peak. The inclined face is defined by a first radius of curvature that transitions to the substantially flat peak. The teeth are spaced circumferentially and spiral around the upper cylindrical shank and a lower cylindrical shank. There is a spring for applying pressure across the upper cylindrical shank and the lower cylindrical shank. The teeth of the upper cylindrical shank and the lower cylindrical shank engage for relative rotation when the handle is turned and disengage when a predetermined value of torque is exceeded.

A fortified plastic connector mount, in accordance with the present disclosure of a device with a plastic nose having a distal and a proximal end, formed as part of or affixed to the flat top of a body; the nose having a polygonal channel guide with corners. The channel formed axial and centered in the nose and of a size to accept a tool or shaft; at least one pair of force buttressing ribs "FBR" wherein said FBR have a bottom affixed at the flat top and the FBR has a support edge affixed to an annular outer wall of the nose; and, wherein the proximal end of the nose is affixed at the flat top. In some instances the channel is square.

A fortified plastic connector mount, in accordance with the present disclosure of a device with a plastic nose having a distal and a proximal end, formed as part of or affixed to the flat top of a body; the nose having a square channel guide with corners. The channel formed axial and centered in the nose and of a size to accept a tool or shaft; four pairs of force buttressing ribs "FBR" wherein said FBR have a bottom affixed at the flat top and the FBR has a support edge affixed to an annular outer wall of the nose; and, wherein the proximal end of the nose is affixed at the flat top. The four pairs of FBR each pair being positioned along one of the four side of the square channel. In some instances, each FBR further comprises an interior edge and an outer edge and each outer edge is aligned with a corner.

A fortified plastic connector mount, in accordance with the present disclosure of a device with an elongated nose with a distal end fluidly connected to an interior channel formed axially therein; a wall with a predetermined thickness surrounding the interior channel with an outer annular surface; a flat top affixed to or formed as part of the proximal end of the nose; and, at least one pair of force buttressing ribs "FBR" (120 & 120') affixed to both the flat top and the annular wall.

A fortified plastic connector mount, in accordance with the present disclosure of a device with an elongated nose with a distal end fluidly connected to a square interior channel, with four corners, formed axially therein; a wall with a predetermined thickness surrounding the interior channel with an outer annular surface; a flat top affixed to or formed as part of the proximal end of the nose; four pairs of force buttressing ribs "FBR" affixed to both the flat top and the annular wall; and, the four pairs of FBR each aligned with one of the four walls of the interior channel.

The above-mentioned features of the present disclosure will become more apparent with reference to the following description taken in conjunction with the accompanying drawings wherein like reference numerals denote like elements and in which:

FURTHER DISCLOSURE

Figure 6:
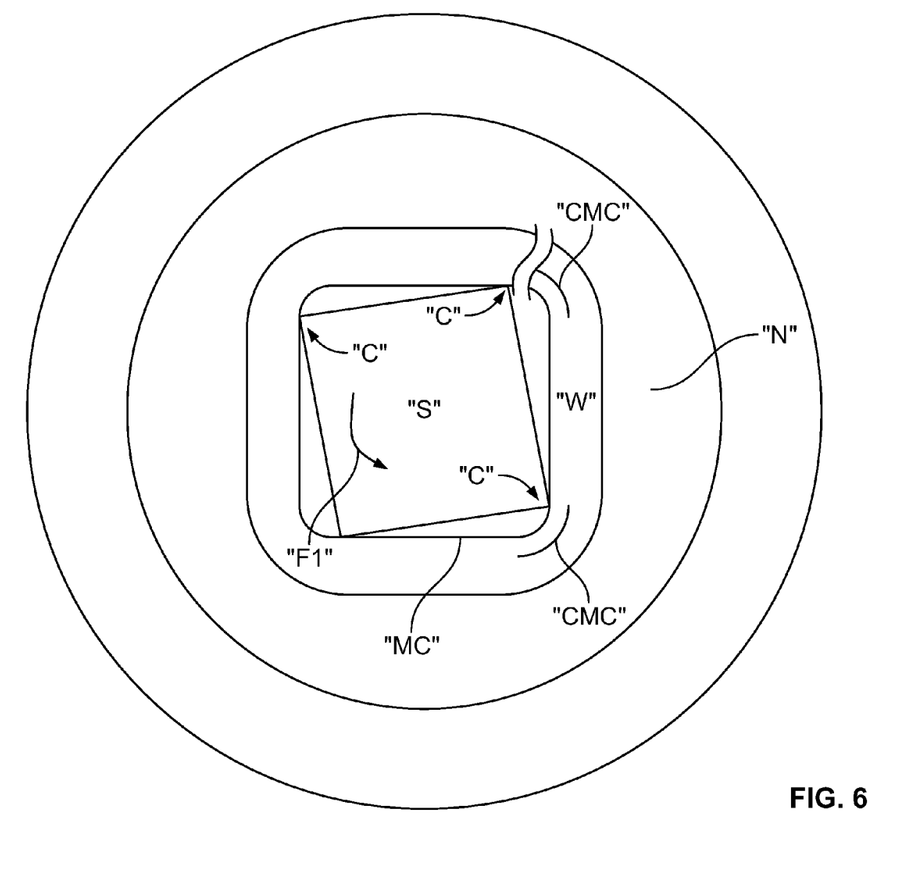
FIG. 6 is a diagrammatic view of how a traditional non-fortified connector mount will fail fails under the same force the fortified mount of FIG. 5 will tolerate.
Figure 7:
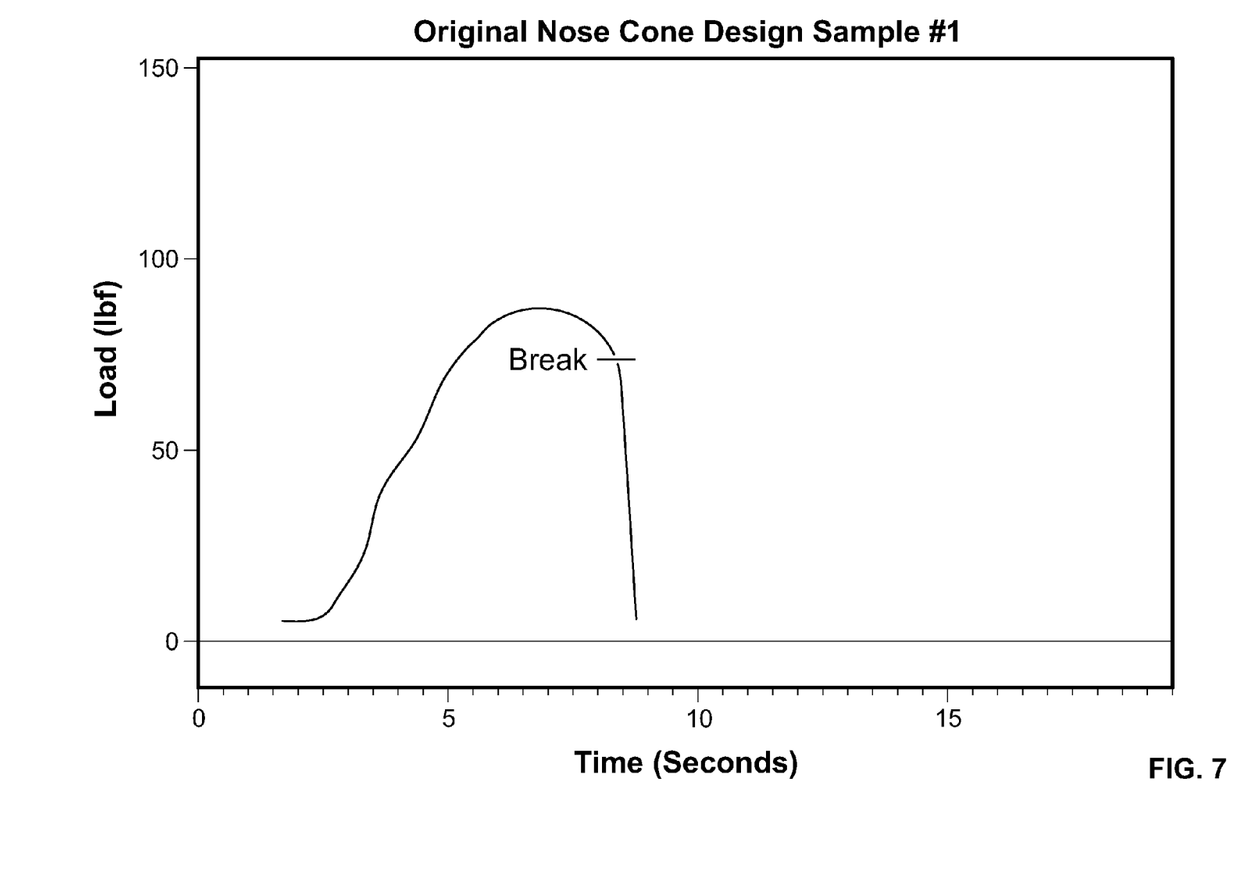
FIGS. 7 and 8 are charts showing test to failure for a traditional mount shown in FIG. 1.
Figure 8:
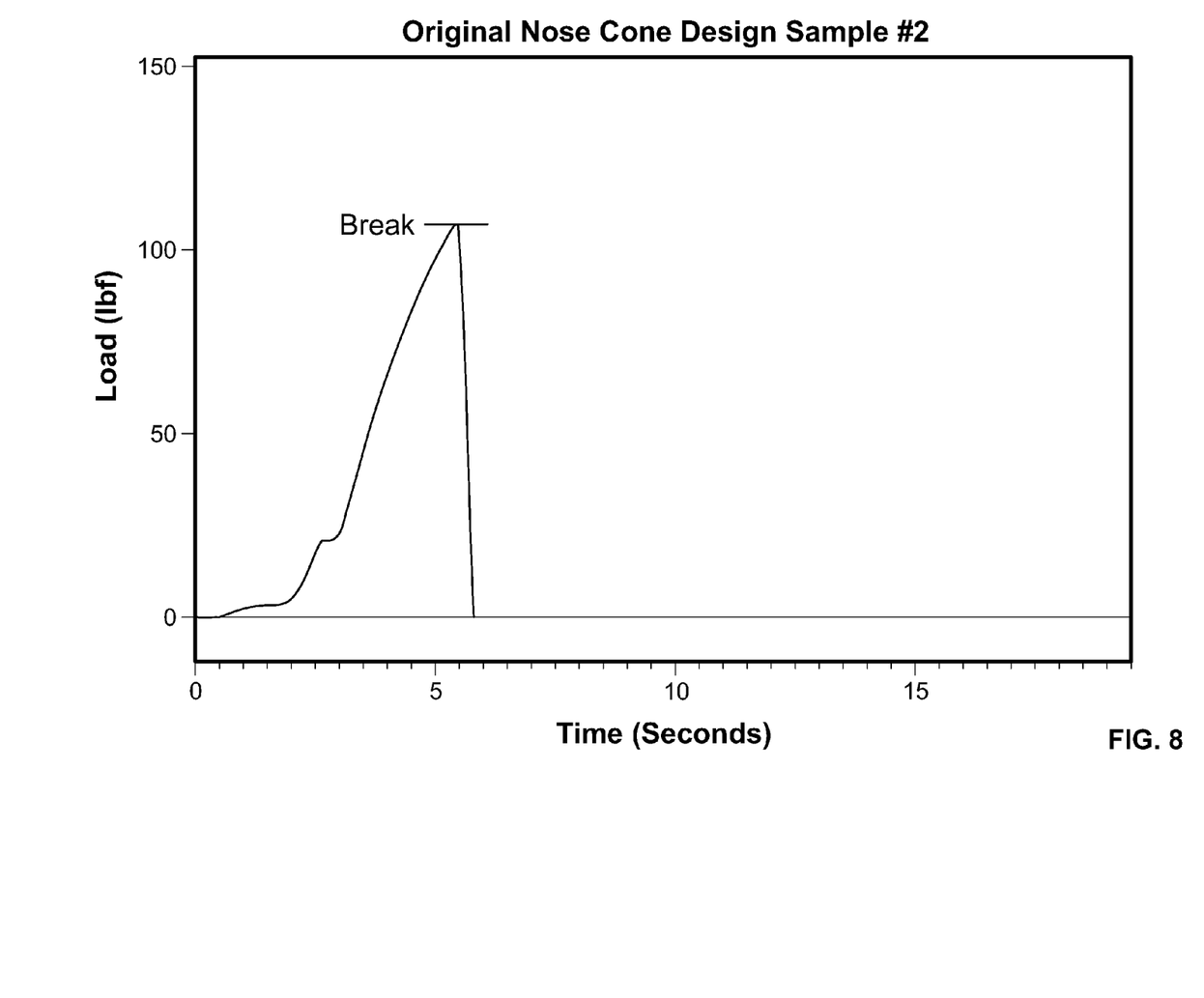

Referring to FIGS. 1, 6, 7 and 8, there is a plastic molded connection mount 5, representative of traditional strength molded mounts for fixing or connecting tools and/or other connectors thereto. The connection mount has a nose 7, a neck 8, and are affixed to body 9. Such mounts are used to provide support for a shaft (not shown) and hold fast a shaft against a force applied via rotation of the nose 7 and body 9. A plurality of support flanges 11 are positioned around a neck 8 to add strength while saving material. A connection mount has at its distal end 13 a guide 15 whereby a tool or shaft (not shown) may be mounted. An annular wall 17 surrounds the connection mount. FIGS. 7 and 8 are findings from two tests to failures of the performance of the traditional molded mount illustrated in FIG. 1.

Referring to FIGS. 2-5, 9 and 10 there is a plastic molded fortified connector mount "CM" 50. The connector mount is a guide and/or anchor to mount, fix or connect tools and/or other connectors to the CM. The CM mount has a generally conical back nose 100, affixed to a body 102. The affixation of nose to body includes molding as a single piece. The body 102 is generally cylindrical and has a flat top 105. The nose back 100 has an annular outer wall 108.

The CM 50 is a support or encasement of a shaft which will hold fast a shaft against a force applied via rotation of the nose 100 and body 102. Even numbered sets of force buttressing ribs (FBR) 120 & 120' are positioned around the outer annular wall 108 of back nose 100. At the distal end 125 of the CM is a channel 150 which acts as a guide whereby a tool or shaft may be mounted. In some instances, the channel is generally square with four sides.

Figure 5:
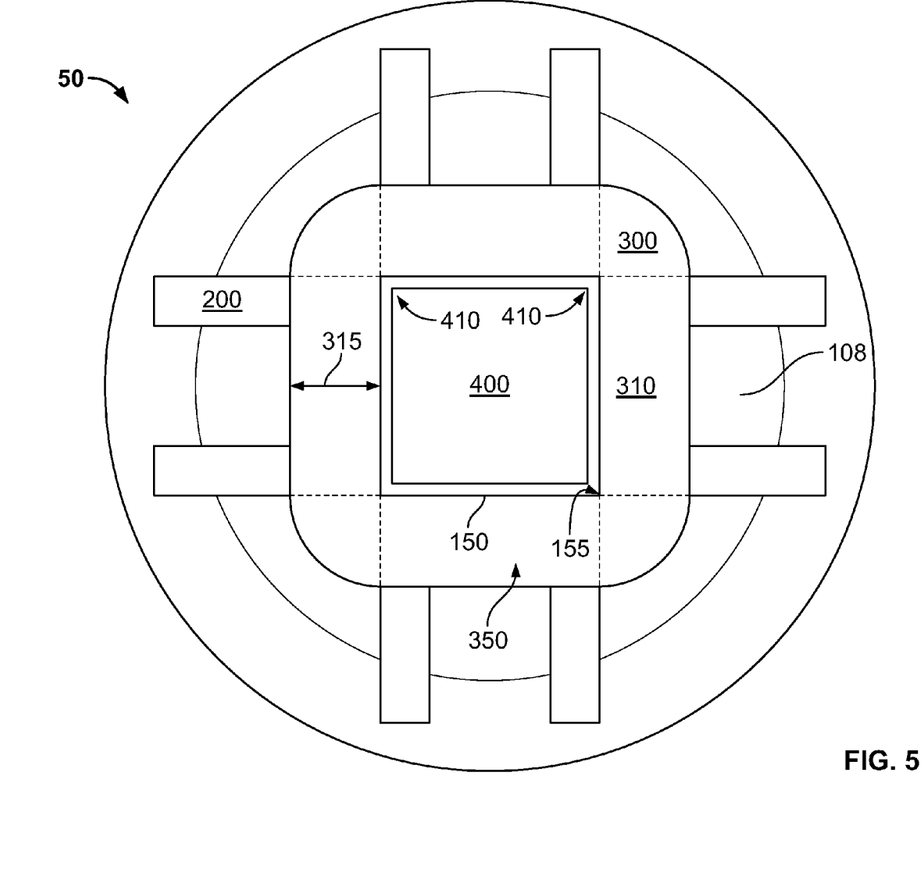
FIG. 5 is a diagrammatic view a fortified connector mount, less susceptible to failure then a traditional mount.

FIG. 5 is a diagrammatic view of the nose in a fortified mount device. When shaft 400 within the drive channel 150, the corners of the shaft 410 are adjacent to the corner channels 155. The drive channel 150 is substantially square. Each channel corner 155 has been shown to be a region where the plastic tends to deform, break or otherwise fail under the rotational forces applied thereto via a rotating shaft 400. The corners 410 of the shaft when rotated against the channel corners 155 have significant impact on the corners and the plastic back nose 100. When shaft 400 within said drive channel 150 is rotated at force one (F1) and force one (F1) is selected to be at the maximum tolerance of the fortified connector mount an un-fortified drive channel 150 will break deform and fail in less time and under/or under less force than a fortified connector mount 50. Ribs 200, support the connection mount, and prevent the wall structure, especially at the corners 410 of the nose from at least one of deforming, distorting and breaking due to failure under F1.

In the unfortified nose illustrated in FIG. 6 failure will occur as follows: The shaft "S" within a mount channel "MC" is rotated at a force which is within the operational tolerance of the disclosed fortified connector mount of FIGS. 2-5 the similar sized non-fortified mount will distort, deform and/or break the wall "W" of the nose "N". Or stated in another way, in the absence of the strategically placed FBRs when force one (F1) is applied the mount channel will fail. The corners "C" of the shaft "S" when rotated against the corner of the mounting channel "CMC" have the most significant impact of force upon the back nose. It is at those CMC locations of the MC where there is the greatest possibility of a fortified wall will crack. The crack can occur because the opposite side of the wall at the corners does not have any bracing. Moreover, a thicker wall "W" would not make the wall any stronger or less likely to crack, but may, in fact, make it weaker. When enough force is applied to the opening of the nose cone, the walls of the nose "N" can deflect. If the nose wall deflects enough, a crack can occur and testing has shown that a thicker wall may crack under less force.

Figure 1:
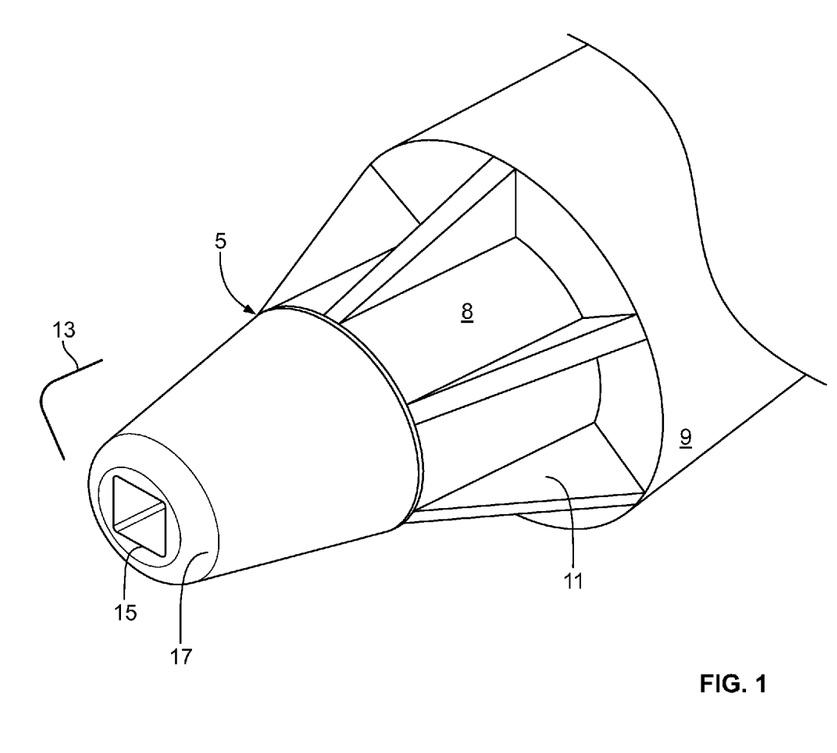
FIG. 1 is a perspective view of a traditional connector mount.
Figure 2:
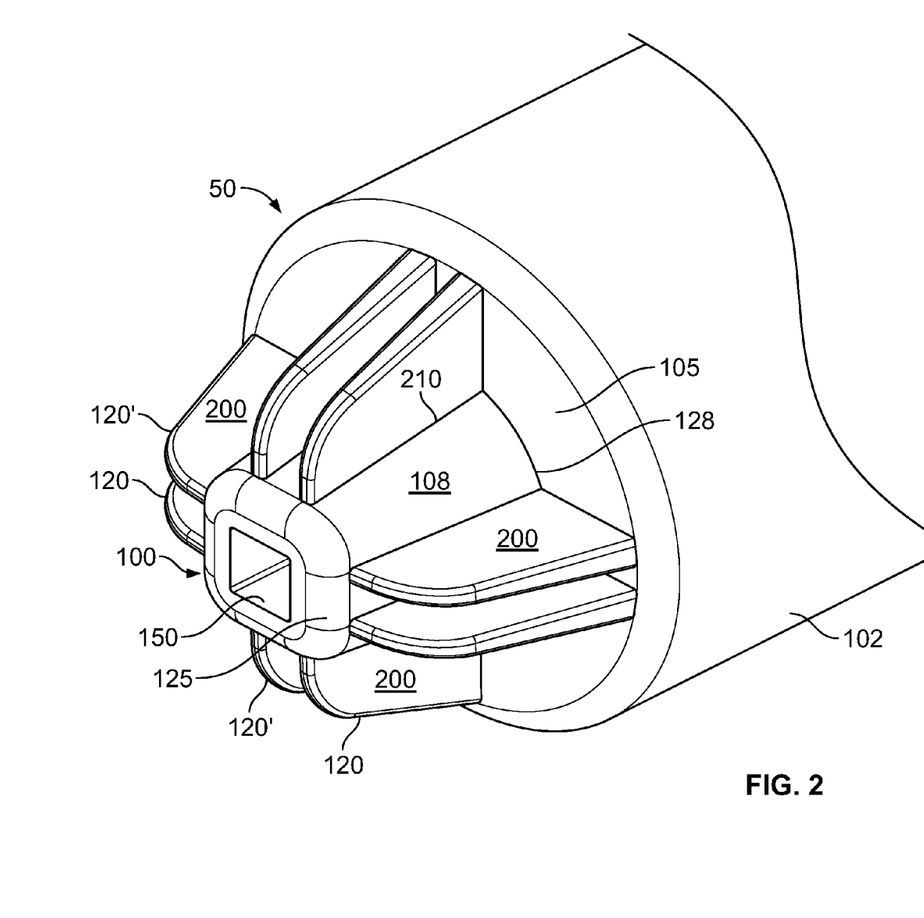
FIG. 2 is a perspective view of a fortified connector mount in accordance with the present disclosure.
Figure 3:
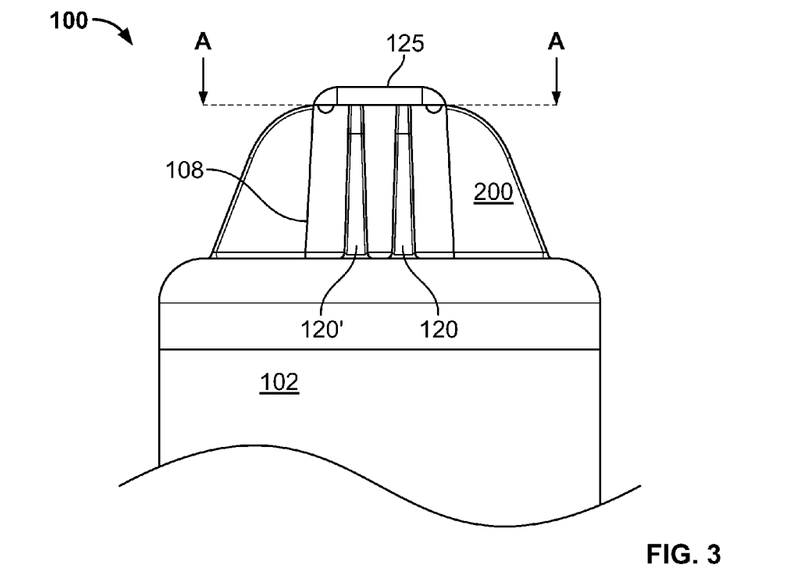
FIG. 3 is a side view of a fortified connector mount in accordance with the present disclosure.
Figure 4:
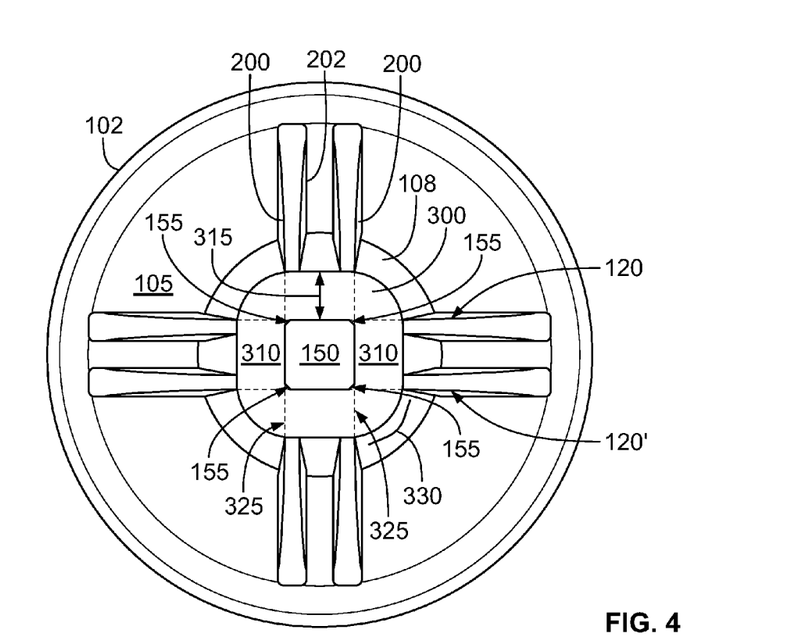
FIG. 4 is a cut away along line "A-A" top perspective view of a fortified connector mount in accordance with the present disclosure.

In the disclosed fortified mounting the back nose 100 is fortified or buttressed against shearing and other forces via very specifically placed ribs 120 & 120'. The wall structure 350 of the back nose between the annular outer wall 108 and the channel 150 is separated into alternating zones. Each zone is separated by a fortification. Zone 1 is the corner zone 300, zone 2 is the boundary wall zone 310 and the fortifications 325 are areas of the plastic molded back nose 100 which are located substantially directly between each channel corner 155, the annular wall 108 and the outer edge 200 of each rib Boundary wall zone 310 is substantially the same thickness 315 from drive channel 150 to the annular wall 108. That thickness will vary as one moves from the distal end 125 of the nose toward the flat top 105. However, the thickness of boundary wall 310 is substantially the same cross section between fortifications 325. The back nose 100 has a proximal end 128 which is affixed to, formed as part of or mounted to the flat top 105 of the body. In some instances the distal end of the nose 125 is generally squareish with rounded or radiused corners 330 in cross section, and the proximal end is generally circular in cross section. In other instances both the distal end of the nose 125 and the proximal end 128 may be generally squareish with rounded or radiuses corners in cross section. In the wall structure 350 the force buttressing ribs (FBR) 120 & 120' are pairs have a bottom edge 201 which is affixed to, or formed as part of or mounted to the flat top 105 of the body and also have interior edges 202 and outer edges 200. The FBR is attached, affixed, or formed as part of the back nose 100 on the annular wall 108 of the nose at the FBR support edge 210.

FBRs are positioned to be aligned with an edge or side of the drive channel 150 opening, as well as each corner 155. The FBR brace each corner whether the unit is being rotated clockwise or counter-clockwise, so the FBR is preferably inline with each side of each corner. These FBRs are at 90-degrees apart due to being at 180-degrees to the side of each opening they support. Being at 90-degrees and 180-degrees ensures that each side wall zone 310 and each corner zone 300 is equally braced.

FBRs may be positioned at angles other than 90-degrees or 180-degrees, however, there will be an unbalanced situation where one side could be weaker than the other side, and therefore not reinforcing the adjacent zone adequately to withstand the highest force requirement. Such other angles may be acceptable in lower force situation and are within the scope of this disclosure for such situations. A plastic nose material will eventually crack if force beyond the limits of the use intended is applied. By placing each FRB at a 90-degree angle from its base, the 90-degree angle achieves a balance force load, so that each side of rib receives equal force and therefore eliminates the unbalance.

Figure 9:
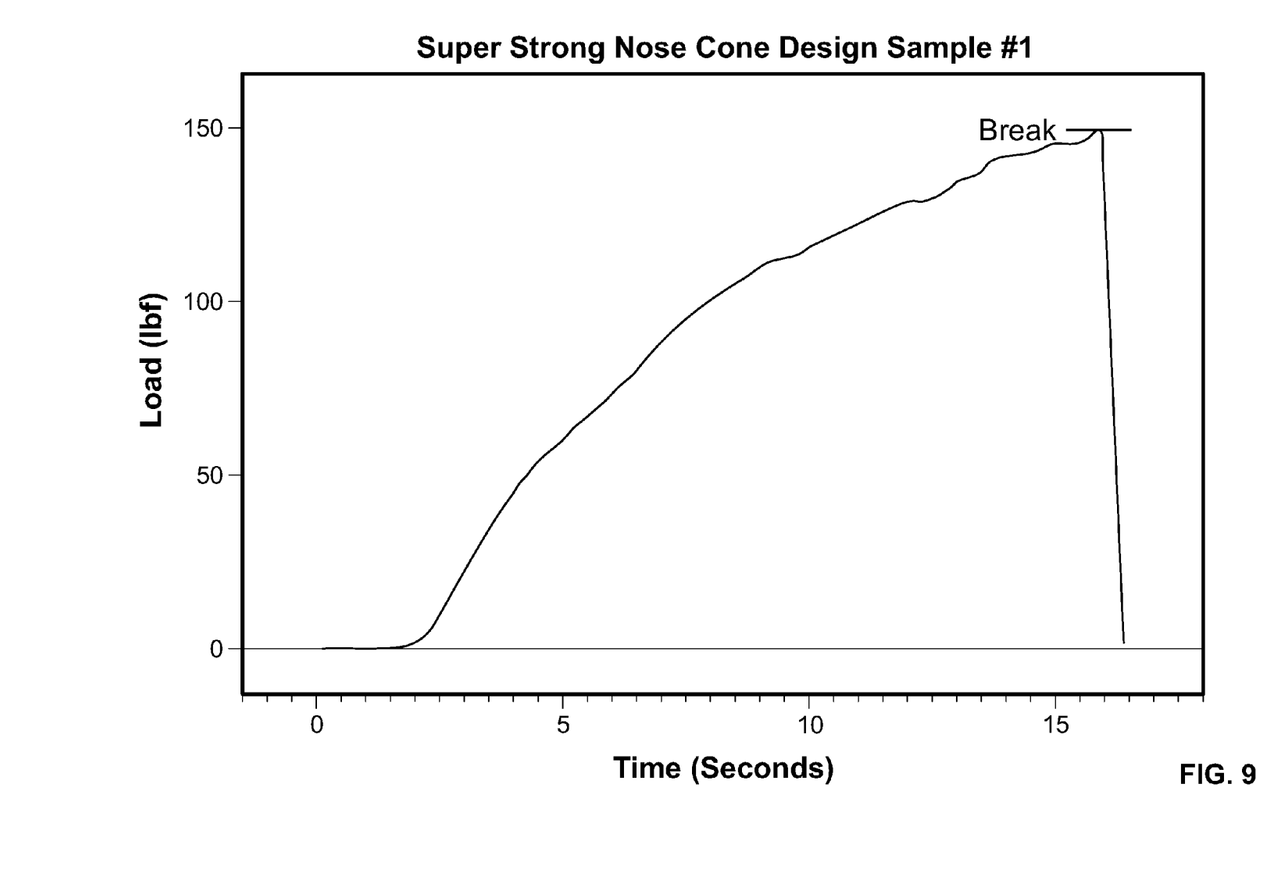
FIGS. 9 and 10 are charts showing test to failure of the fortified mount of FIGS. 2-4.
Figure 10:
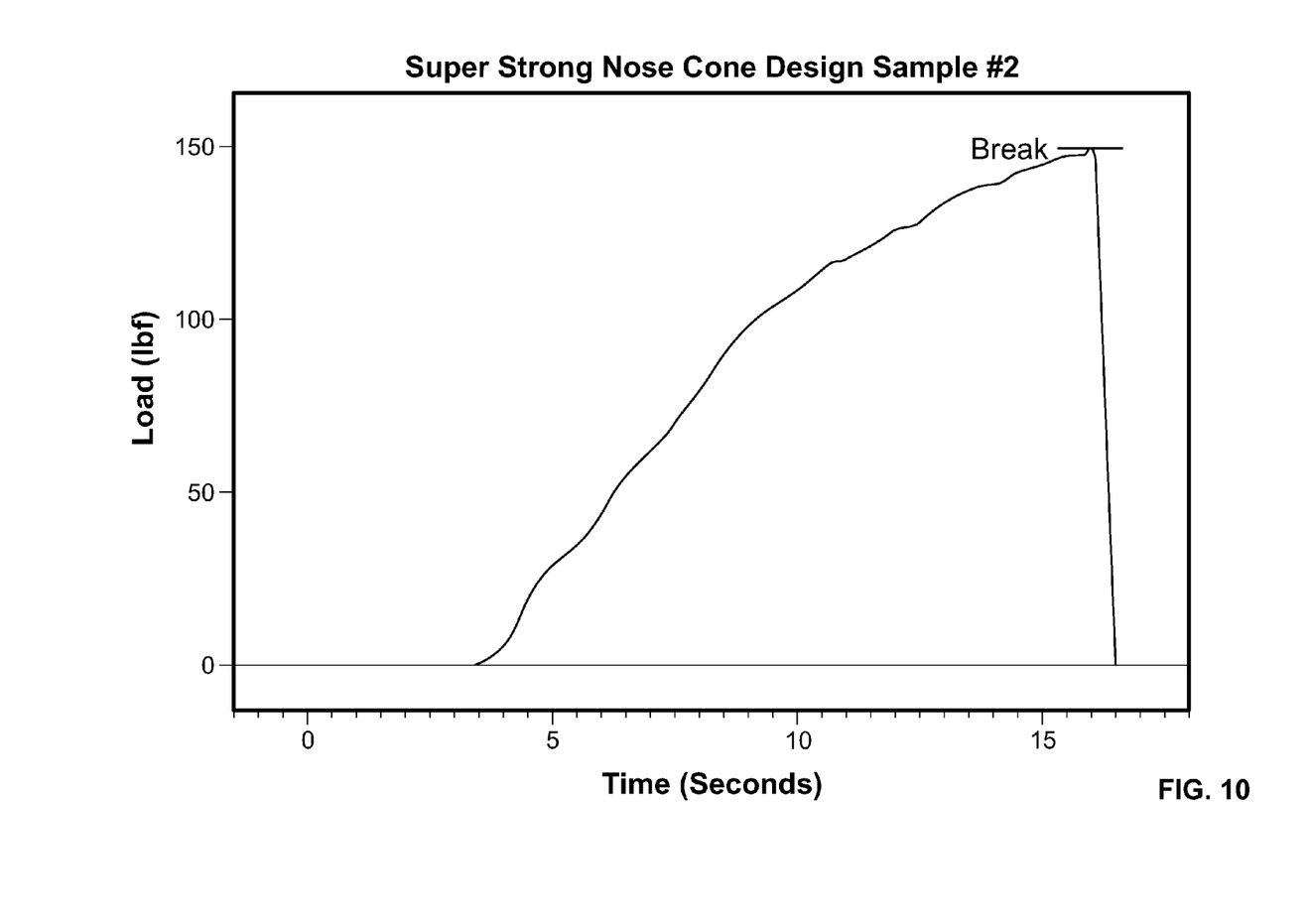

FIGS. 7 and 8 are measurements of a non-fortified connector mount tested to failure. Failure occurs at a load between 115 and 85 lbf and between 7 and 8 seconds. FIGS. 9 and 10 are measurements of a fortified connector mount tested to failure. Failure occurs at a load between 140 and 150 lbf and between 17 and 18 seconds.

While the method and apparatus have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these disclosure(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A plastic connector mount (50) comprising:
    a nose (100) with a proximal end (128) formed as part of or affixed to the flat top (105) of a body (102);
    at least four pairs of force buttressing ribs (120 & 120');
    each force buttressing rib has an interior edge (202) and an outer edge (200) and each outer edge is aligned with a corner (155);
    each member of the force buttressing rib pair is aligned with a corner; and,
    the outer edges of two adjacent pairs of force buttressing ribs align with the same corner with each oriented 90 degree apart;
    a distal end (125) of a back nose (100); and
    a square channel (150) guide having corners (155), the square channel formed axial and centered in the back nose of a size to accept a tool or shaft;

wherein said force buttressing ribs each have a bottom (201) affixed at the flat top and each force buttressing rib has a support edge (210) affixed along the length of the back nose.

2. The connector mount of claim 1 wherein there are four pairs of force buttressing ribs, each pair being positioned along one of the four sides of the square channel.

3. A method of fortifying a connector mount, the method comprising:
- forming an annular wall (108) around a square channel (150) of the connector mount, the annular wall being generally squarish with radiused corners;
- supporting load on the connector mount with four pairs of force buttressing ribs (120 & 120'), whereby pairs of force buttressing ribs are positioned along each flat portion of the annular wall (310) and load from the shaft (400) exerted on the annular wall is transferred to a flat top (105) of the connector mount;
- one force buttressing rib of each pair is placed at each corner whereby there are two force buttressing ribs at each corner separated by a 90 degree offset;
- wherein each force buttressing rib is aligned with a corner (155) of the square channel of the connector mount; and,
- whereby the connection mount holds the shaft without failure at a load between a force (F1) of 85 and 115 pound-feet for a predetermined time.

4. The method of claim 3, wherein the predetermined time is at least 8 seconds.

5. The method of claim3, wherein the predetermined time is at least 9 seconds.

6. The method of claim 3, wherein the predetermined time is at least 10 seconds.

7. The method of claim 3, whereby the connection mount holds the shaft without failure at a load between a force (F1) of 140 and 150 pound-feet for at least 10 seconds.

8. The method of claim 3, whereby the connection mount holds the shaft without failure at a load between 140 and 150 pound-feet for at least 12 seconds.

9. The method of claim 3, whereby the connection mount holds the shaft without failure at a load between 140 and 150 pound-feet for at least 15 seconds.

10. The method of claim 3, whereby the connection mount holds the shaft without failure at a load between 140 and 150 pound-feet for at least 16 seconds.

11. The method of claim 3, whereby the connection mount holds the shaft without failure at a load between 140 and 150 pound-feet for at least 17 seconds.

12. The method of claim 3, wherein a non-fortified mount will at least one of distort, deform, and break the annular wall during the predetermined time in the absence of the strategically placed force buttressing ribs when the force (F1) is applied.

* * * * *